US00PP10845P

United States Patent [19]

Meilland

[11] Patent Number: Plant 10,845

[45] Date of Patent: Mar. 30, 1999

[54] HYBRID TEA ROSE PLANT NAMED 'MEILAVIO'

[75] Inventor: Alain A. Meilland, Antibes, France

[73] Assignee: CP (Delaware), Inc., Wilmington, Del.

[21] Appl. No.: 923,419

[22] Filed: Sep. 4, 1997

[51] Int. Cl.[6] ..... A01H 5/00

[52] U.S. Cl. ..... Plt./140

[58] Field of Search ..... Plt./20, 21, 139, Plt./140

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms attractive long-lasting very double Currant Red blossoms that are quartered. Such blossoms possess no fragrance. The plant exhibits an erect growth habit with very numerous large thorns. The plant exhibits decorative dark green and semi-glossy foliage, as well as good disease resistance. The new variety is particularly well suited for providing attractive ornamentation when grown in a garden setting.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the 'Meirgano' variety (non-patented in the United States) and the 'Tanaloap' variety (non-patented in the United States). The male parent (i.e., the pollen parent) was the 'Ausroyal' variety (non-patented in the United States). The parentage of the new variety can be summarized as follows:

('Meirgano'×'Tanaloap')×('Ausroyal').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long-lasting very double Current Red blossoms that are quartered,
(b) exhibits an erect growth habit with very numerous large thorns,
(c) forms decorative dark green and semi-glossy foliage,
(d) exhibits good disease resistance, and
(e) is particularly well suited for providing ornamentation in the garden.

The very double blossoms are quartered in the sense that the petals of fully open blossoms tend to be arranged in a plurality of zones when viewed from above.

The new variety of the present invention can be readily distinguished from its 'Meirgano', 'Tanaloap' and 'Ausroyal' ancestors in view of its larger blossoms, the strong and sturdy nature of its blossoms, and the more vibrant red coloration of its blossoms that does not fade.

The new variety well meets the needs of the horticultural industry and is especially suited for growing outdoors in gardens and parks to provide distinctive ornamentation.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meilavio' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during July while budded on *Rosa froebelii* understock and growing outdoors at Le Cannet des Maures, Var, France. Dimensions in centimeters are indicated at the bottom of the photograph.

FIG. 12 illustrates a specimen of a flowering stem;

FIG. 14 illustrates a specimen of a leaf with three leaflets—plan view—upper surface;

FIG. 16 illustrates a specimen of a leaf with seven leaflets—plan view—upper surface.

DETAILED DESCRIPTION

Figures 1, 2, 3, 4, 5, 6, 7, 8, 9, 10, 11, 13, 15:
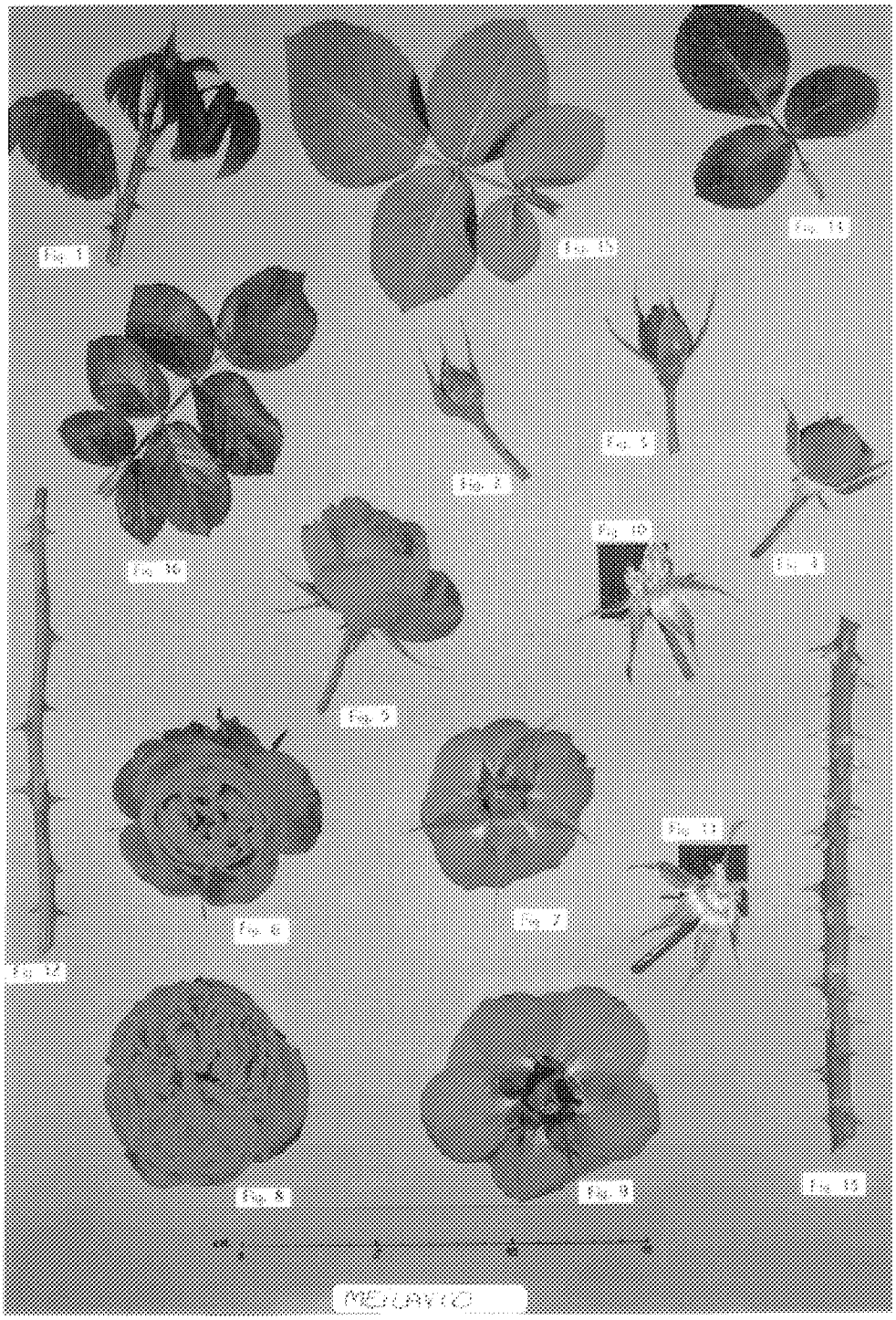
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 13 illustrates a specimen of a main branch.
FIG. 15 illustrates a specimen of a leaf with five leaflets—plan view—under surface.

The chart used in the identification of the colors is that of The Royal Horticultural Society (R.H.S. Colour Chart). The description is based on the observation of two year-old plants during July while budded on *Rosa froebelii* understock and growing outdoors at Le Cannet des Maures, Var, France. The coloration in common terms precedes reference to the chart in some instances.

Class: Hybrid Tea.

Plant:

*Height.*—Approximately 110 to 120 cm.

*Habit.*—Erect.

Branches:

*Color.*—Young stems: Green Group 138A, suffused with reddish coloration. Adult wood: Yellow-Green Group 147B suffused at some locations with reddish-brown coloration.

*Thorns.*—Size: large. Quantity: very numerous. Color: on young stems greenish (Yellow-Green Group 151D) with a reddish base, and on adult stems Greyed-Orange Group 164A.

Leaves:

*Stipules.*—Adnate, pectinate, and moderately large.

*Petioles.*—Upper surface: medium green (Yellow-Green Group 146B) with reddish coloration and glandular in nature. Under surface: light green (Yellow-Green Group 146D), and bear some small thorns.

*Leaflets.*—Number: 3 (most often), 5, and 7. Shape: elliptic. Serration: regular (as illustrated). Texture: leathery. General appearance: dense, dark green, and semi-glossy. Color (young foliage): Upper surface: Green Group 139A, and widely tinted with reddish coloration. Under surface: Green Group 139A, and widely tinted with reddish coloration. Color (adult foliage): Upper surface: dark green, Green Group 131A. Under surface: light green, Green Group 137A.

Inflorescence:

*Number of flowers.*—Usually two to five flowers per stem.

*Stem length.*—Commonly approximately 45 to 60 cm.

*Peduncle.*—Yellow-Green Group 144A in coloration, grandular, and the length is approximately 6 cm. on average.

*Sepals.*—Upper surface: reddish-green in coloration. Under surface: Yellow-Green Group 144A in coloration and commonly possess few or no extensions.

*Buds.*—Shape: globular. Size: large. Length: approximately 2 cm. on average. Color upon opening: Upper surface: Red Group 46A. Under surface: Red Group 46A.

*Flower.*—Shape: hollow cup with a generally flat center. Diameter: approximately 6.5 to 7 cm. on average. Color (when opening begins): Upper surface: Currant Red, Red Group 46A. Under surface: Greyed-Red Group 179A. Color (when blooming): Upper surface: velvet Currant Red, near Red Group 46A. Under surface: Currant Red, near Red Group 47A. Color (at end of opening): Upper surface: near Red Group 45A. Under surface: Currant Red, near Red Group 47A. Fragrance: none. Lasting guality: very long. The blossoms commonly last approximately 10 to 14 days on the plant and approximately 14 days when cut and placed in a vase. Petal number: very double, commonly approximately 100 to 110 on average. Petal shape: the base is cordiform and the tip is somewhat rounded. Petal drop: the petals commonly detach cleanly. Stamen number: approximately 174 on average. Anthers: Yellow-Orange Group 14B in coloration. Filaments: Orange-Red Group 33B in coloration. Pistils: approximately 153 on average. Stigmas: yellowish in coloration. Styles: light yellow (Yellow Group 8D) with brown tones at the tip. Receptacle: light green, sometimes stained with brownish coloration, and in longitudinal section in the shape of a pitcher.

Development:

*Vegetation.*—Strong.

*Blooming.*—Abundant.

*Resistance to diseases.*—Very good with respect to black spot and powdery mildew.

I claim:

1. A new and distinct variety of Hybrid Tea rose plant characterized by the following combination of characteristics:

(a) forms attractive long-lasting very double Currant Red blossoms that are quartered,
(b) exhibits an erect growth habit with very numerous large thorns,
(c) forms decorative dark green and semi-glossy foliage,
(d) exhibits good disease resistance, and
(e) is particularly well suited for providing ornamentation in the garden.

substantially as herein shown and described.

* * * * *